US00PP23025P3

(12) United States Plant Patent
Harris

(10) Patent No.: US PP23,025 P3
(45) Date of Patent: Sep. 11, 2012

(54) AZALEA PLANT NAMED 'MNIHAR015'

(50) Latin Name: ***Rhododendron* sp.**
Varietal Denomination: MNIHAR015

(75) Inventor: James O. Harris, Lawrenceville, GA (US); Ella Ruth Harris, legal representative, Lawrenceville, GA (US)

(73) Assignee: Ella Ruth Harris, Lawrenceville, GA (US), Executor of the Estate of James O. Harris ( * ) Notice: Subject to any disclaimer, the term of this patent is extended or adjusted under 35 U.S.C. 154(b) by 142 days.

(21) Appl. No.: 12/807,037

(22) Filed: Aug. 25, 2010

(65) Prior Publication Data

US 2012/0054931 P1 Mar. 1, 2012

(51) Int. Cl.
*A01H 5/00* (2006.01)

(52) U.S. Cl. ..... Plt./240

(58) Field of Classification Search ..... Plt./240, Plt./239

See application file for complete search history.

*Primary Examiner* — June Hwu

(74) *Attorney, Agent, or Firm* — Jondle & Associates, P.C.

(57) ABSTRACT

A new and distinct variety of Azalea plant with spring and fall blooming, attractive, showy, semi-double dark pink flowers, easily propagated by semi-hardwood cuttings in late spring through summer, moderate growth rate under normal fertilization and moisture conditions; broadly-rounded and freely-branching in habit, grows well in containers, thrives in shade or sun and is hardy in Zone 6, is disclosed.

2 Drawing Sheets

Genus and species: *Rhododendron* sp.
Variety denomination: 'MNIHAR015'.

BACKGROUND OF THE NEW PLANT

The present invention is a new and distinct variety of evergreen Azalea of the genus *Rhododendron*. This new Azalea, hereinafter referred to as 'MNIHAR015', was discovered in 2004 in Lawrenceville, Ga. 'MNIHAR015' originated from a planned cross hybridization in 1998 between the female azalea plant 'Conleb' (U.S. Plant Pat. No. 10,581) and the male azalea plant 'Helen Close' (unpatented) in a controlled environment in Lawrenceville, Ga. The present invention has a unique combination of blooming period, growth habit, and cold hardiness.

The new plant was first propagated via semi-hardwood cuttings in 2004 in Dearing, Ga. and has been asexually reproduced repeatedly by semi-hardwood cuttings in Dearing, Ga. for over six years. The new plant retains its distinctive characteristics and reproduces true to type in successive asexual propagations by semi-hardwood cuttings.

Plant Breeder's Rights for 'MNIHAE015' have not been applied for. 'MNIHAR015' has not been made publicly available or sold more than one year prior to the filing date of this application.

SUMMARY OF THE INVENTION

The following are the most outstanding and distinguishing characteristics of this new plant when grown under normal horticultural practices in Dearing, Ga.

1. Spring and fall blooming;
2. Attractive, showy, dark pink colored flowers;
3. Numerous semi-double flowers;
4. Easily propagated by semi-hardwood cuttings in late spring through summer;
5. Moderate growth rate under normal fertilization and moisture conditions;

6. Rounded, compact in nature;
7. Grows well in containers;
8. Thrives in shade or sun; and
9. Hardy in Zone 6.

DESCRIPTION OF THE PHOTOGRAPHS

This new Azalea plant is illustrated by the accompanying photographs which show buds, flowers, immature foliage and mature foliage. The colors shown are as true as can be reasonably obtained by conventional photographic means. The photographs are of 4-year old plants grown in filtered shade in September in 2009 in Dearing, Ga.

DETAILED BOTANICAL DESCRIPTION OF THE NEW PLANT

Figure 1:
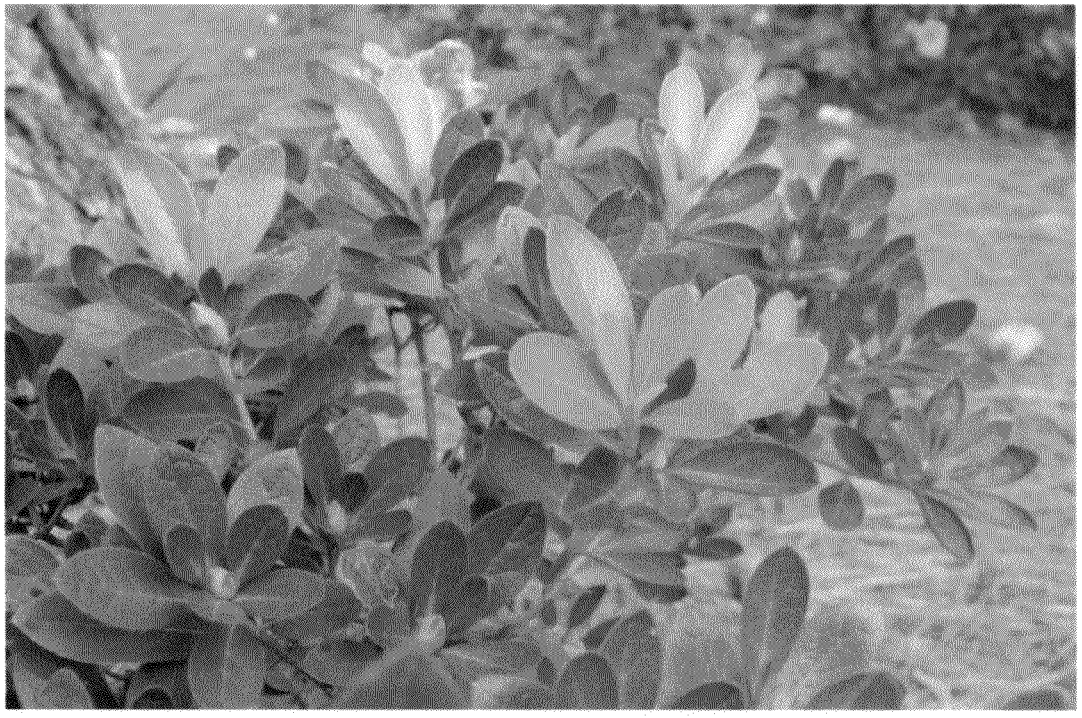
FIG. 1 is a close-up showing the stems and mature foliage.
Figure 2:
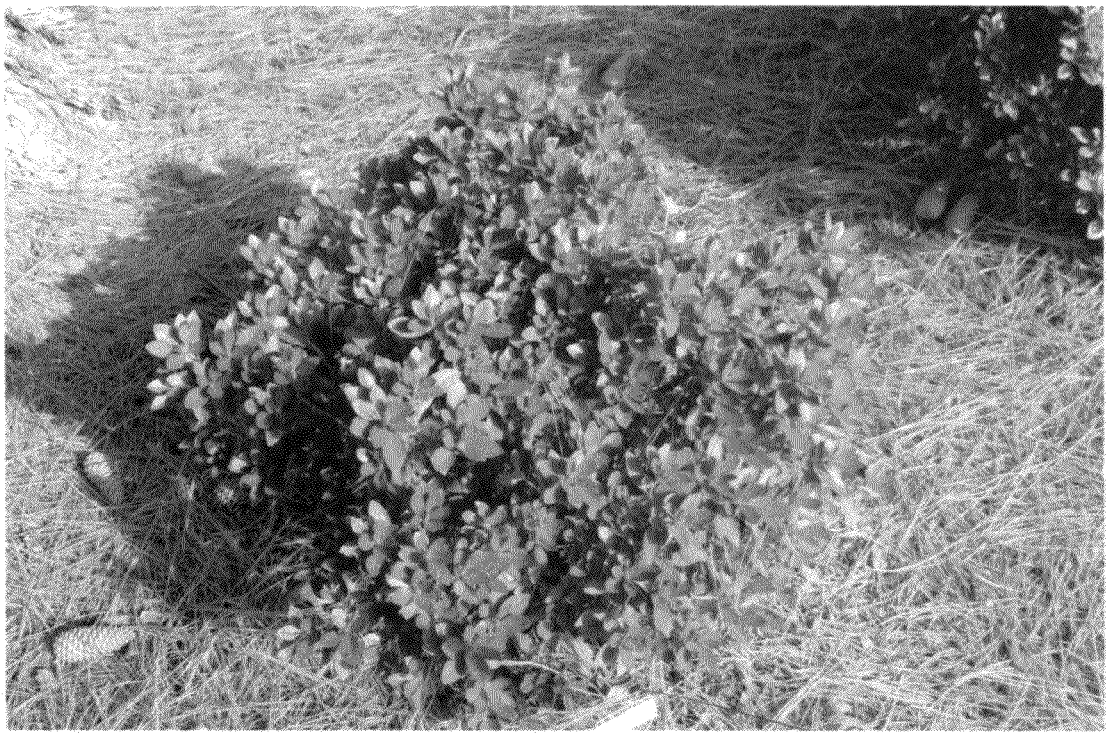
FIG. 2 shows the mature foliage and growth habit of a 5-year old plant.
Figure 3:
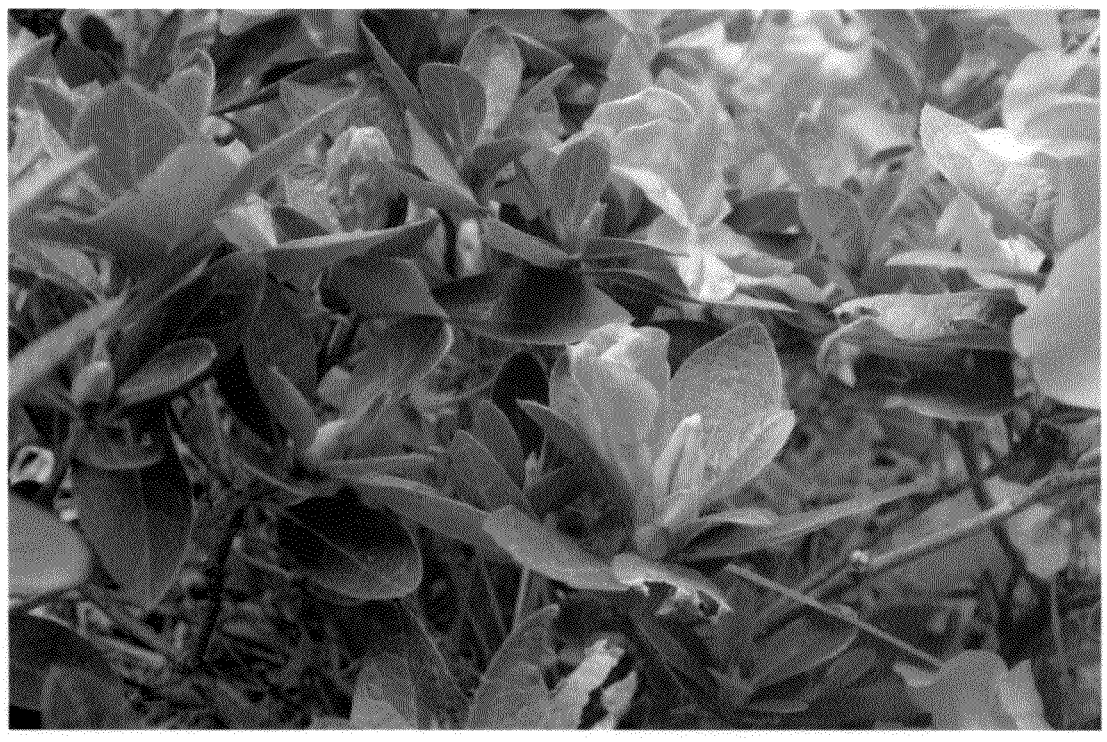
FIG. 3 is a close-up showing flower buds and immature foliage.
Figure 4:
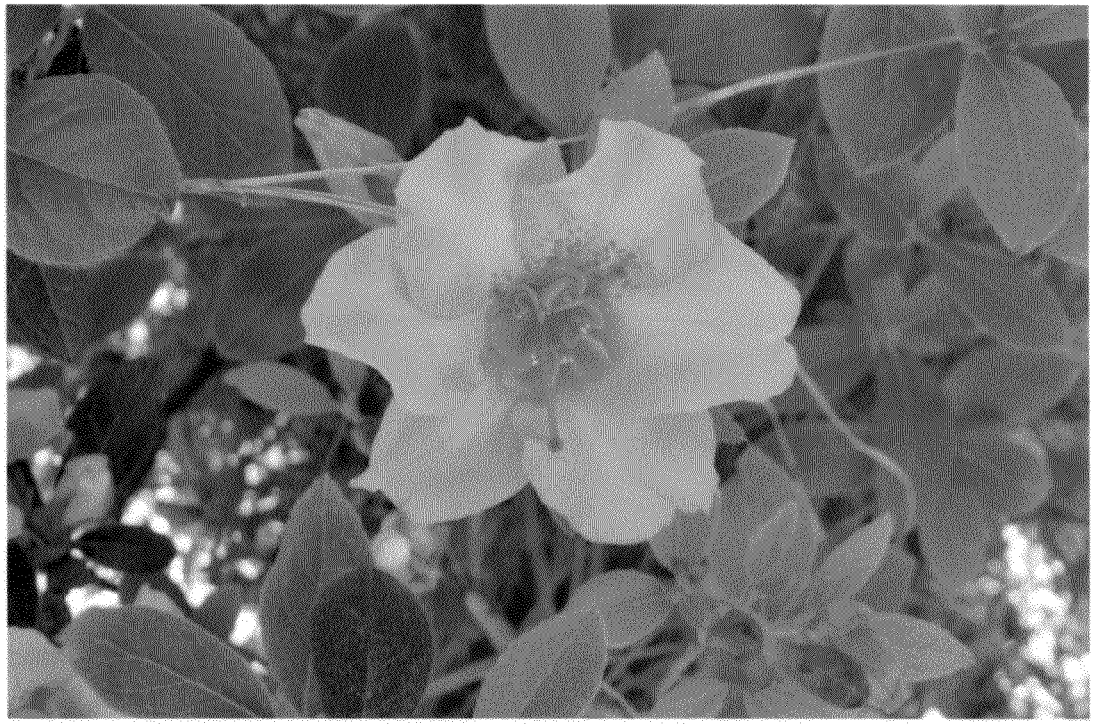
FIG. 4 is a close-up showing flower size, form, and color.

The following is a detailed description of the new Azalea plant based on observations made of 4-year-old plants grown in a three-gallon containers according to wholesale commercial production conditions under full-sun and in an evaluation bed under semi-shade conditions in Dearing, Ga. in spring, summer, and fall in 2009. The colors of the various plant parts are detailed with reference to The Royal Horticultural Society Colour Chart (2001).

Classification:

*Family*.—Ericaceae.
*Species*.—*Rhododendron* sp.
*Common name*.—Azalea.
*Commercial name*.—'MNIHAR015'.

Parentage:

*Female parent*.—The azalea plant 'Conleb' (U.S. Plant Pat. No. 10,581).

*Male parent*.—The azalea plant 'Helen Close' (unpatented).

Growth:

*Form*.—Rounded, compact in nature.

*Texture*.—Medium.

*Height*.—76.2 cm to 106.68 cm.

*Width*.—106.68 cm to 121.92 cm.

*Growth habit*.—Rounded and freely-branching.

*Growth rate*.—Moderate growth rate under normal fertilization and moisture conditions. In a period of five years from a rooted cutting the plant reaches a height of 40.64 cm and a spread of 71.12 cm. The growth rate normally averages about 3.6 cm per year; the plant reaches a height of 76.2 cm to 106.68 cm at maturity while maintaining a dense habit due to the abundant branch development.

*Spring growth*.—The date of initial spring growth is March 20, followed by continuous growth through fall.

*Life cycle*.—Perennial and evergreen.

Leaves:

*Arrangement*.—Alternate, simple, pubescent, and evergreen.

*Shape*.—Elliptic.

*Apex*.—Mucronate.

*Base*.—Acuminate.

*Margin*.—Entire.

*Length*.—3.5 cm.

*Width*.—1.5 cm.

*Venation pattern*.—Pinnate; the mid-veins and laterals are impressed on the upper surface and the prominent on the lower surface.

*Venation color* (*both surfaces*).—RHS 144A (yellow-green).

*Immature leaf*.—Upper surface: Color: Matte, RHS 144A (yellow-green). Pubescence: Strigose, low to moderate amount; color is RHS N155A (white) to RHS 159B (orange-white). Lower surface: Color: Matte, RHS 146C (yellow-green). Pubescence: Strigose, moderate amount mainly along mid-vein; color is RHS 155C (white).

*Mature leaf*.—Upper surface: Color: Matte to Semi-glossy, RHS 147A (yellow-green). Pubescence: Villous; color is RHS 164D (grey-orange). Lower surface: Color: Matte, RHS 146A (yellow-green). Pubescence: Villous; color is RHS 164B (greyed-orange).

*Petiole*.—Length: 0.4 cm to 0.6 cm. Diameter: 0.15 cm by 0.1 cm. Pubescence: Villous and hirsute becoming strigose, length is 0.15 cm to 0.3 cm and color is RHS N155A (white) and RHS 159A (orange-white) and maturing to RHS 161C (greyed-yellow). Color: Begins as RHS 142B (green) and matures to RHS 144A (yellow-green).

Stems:

*Form*.—Densely branched at buds.

*Young stems* (1-*year old and younger*).—Color: RHS N144D (yellow-green) maturing to RHS N199C (grey-brown). Pubescence: Strigose RHS 164C (greyed-orange) to RHS 165A (greyed-orange).

*Second-year stems*.—Stem and pubescence color: RHS 197B (greyed-green) with strigose pubescence RHS 197B (greyed-green) present. Length: 10 cm on average. Diameter: 0.3 cm. Pith: Solid and uniform. Internode length: Average 1.7 cm.

Flower buds:

*Arrangement and form*.—Tight; borne in groups of one or two with some in groups of four and five sheathed by a pair of modified leaf bracts which are 1.3 cm in length, 1.0 cm in width, persistent and RHS 144A (green) in color.

*Shape*.—Ovate.

*Apex*.—Acuminate.

*Base*.—Rounded.

*Length* (*at tight bud*).—1.3 cm.

*Diameter* (*at tight bud*).—0.3 cm.

*Bud scales*.—Length: 1.2 cm. Width: 0.4 cm.

*Color* (*of scales*).—Immature scales are RHS 142C (green) and mature to RHS 145A (yellow-green).

*Texture*.—Scabrous; strigose pubescence RHS 164A (greyed-orange).

*Pedicel*.—Length: 0.8 cm. Diameter: 0.15 cm. Texure: Strigose pubescence that is RHS N155A (white). Color: RHS 182A (greyed-red).

*Calyx*.—Form and arrangement: Composed of 5 sepals in a cup-shape. Length: 0.65 cm. Width: 0.65 cm. Color: RHS 144A (yellow-green). Pubescence: Strigose; RHS N155A (white) in color with a RHS 58A (red-purple) apex. Sepals: Shape: Broadly elliptical. Apex: Cuspidate to Obtuse. Base: Fused; joined at base to form a cup. Margin: Entire with some lobulate. Color: Upper surface: RHS 144A (yellow-green). Lower surface: RHS 143C (green). Length: 0.8 cm. Width: 0.35 cm.

Flowers:

*Type*.—Perfect, Semi-double flowers.

*Shape*.—Open funnel-shaped.

*Flowering habit and period*.—Borne on the current season's growth; two weeks beginning in late March in Dearing, Ga.; flowering resumes in late August and continues until frost which can be as late as November or December.

*Lastingness of flowers on the plant*.—4 to 6 days in the sun; 4 to 7 days in the shade; flowers are self cleaning.

*Fragrance*.—Absent.

*Diameter*.—5.0 cm.

*Depth*.—3.2 cm.

*Petals*.—Quantity per flower and arrangement: 5 or 6 imbricate petals of the corolla tube that are fused at the base and remain fused up to 1.5 cm from the base and 1.9 cm from the base for the three petals with spots. Shape: Obovate. Apex: Rounded. Base: Fused. Margin: Entire to undulate. Texture (both upper and lower surfaces): Glabrous. Length (of petals without spots): 3.2 cm. Width (of petals without spots): 2.0 cm. Length (petals with spots): 1.8 cm. Width (petals with spots): 3.0 cm. Color: upper surfaces are RHS 64D (red-purple); lower surfaces are RHS 62B (red-purple); the upper surface of the spots are RHS 71A (red-purple) and lower surface of spots are not visible.

*Petaloids*.—Length: 1.5 cm. Width: 0.9 cm. Shape: Slightly obovate, apex irregularly rounded, lobed and notched. Color: RHS 64D (red-purple).

Reproductive parts:

*Pistil*.—Quantity and form: Single, non-petaloid. Length: 3.8 cm. Diameter: 0.1 cm. Stigma: Color: RHS N167B (greyed-orange). Diameter: 0.15 cm.

Style color: RHS 47D (red). Ovary: Pubescent, Strigose RHS N155A (white), with 5 locules.

*Stamens*.—Number: 5 to7 per flower; petaloid. Length: 1.6 cm. Color: RHS 51B (red). Filament: RHS 51B (red); 1.6 cm in length. Anther: RHS 167C (greyed-orange); 0.2 cm in length by 0.1 cm in width. Pollen: Abundant; RHS 155D (white).

Fruit:

*Maturity*.—The capsule matures in about 6 months in Dearing, Ga. and the fruit set is low and contains about 100 to 300 non-winged seeds.

*Length*.—0.6 cm.

*Width*.—0.5 cm.

*Color*.—RHS 147B (yellow-green).

CULTURE

'MNIHAR015' grows well in a wide range of conditions and tolerates sun to shade. 'MNIHAR015' prefers moist, well-drained soil that is rich in organic matter and responds well to mulching and medium applications of fertilizer. 'MNIHAR015' does best in soil with a pH of 5.0 to 5.5 and is propagated with semi-hardwood cuttings in late spring through the summer. Azaleas root in five to six weeks with high 80% plus percentage of rooting, tissue culture is also an effective means of propagation for azaleas.

DISEASES AND INSECTS

Lace bugs, root weevils, and spider mites can be a problem. Fungal and bacterial pathogens have not been observed, but no resistance testing has been performed and no claim to abnormal resistance to pathogens can be made.

COMPARISON WITH PARENTAL AND COMMERCIAL VARIEITES

In Table 1, 'MNIHAR015' is compared to parental varieties 'Conleb' (U.S. Plant Pat. No. 10,581) and 'Helen Close' (unpatented) and lists the differences between the varieties.

TABLE 1

| Characteristic | 'MNIHAR015' | 'Conleb' | 'Helen Close' |
|---|---|---|---|
| Plant Height (Mature) | 76.2 cm to 106.68 cm | 121.92 cm to 152.4 cm | 121.92 cm |
| Flower Diameter | 5 cm | 6.5 cm | 7.62 cm |
| Flower Form | Semi-double | Single to semi-double | Single |
| Flower Color | Dark Pink | Red | White with pale yellow blotch |
| Bloom Period | Late-March to April and late August until frost | April and late July until frost | Mid April to May |
| Hardy Zone | 6 | 7 | 6 |
| Stamen Number | 5 to 7 | 0 to 9 | 3 to 8 |
| Stamen Type | Petaloid | Petaloid and Non-petaloid | Non-petaloid |

When 'MNIHAR015' is compared to the commercial variety 'Roblen' (U.S. Plant Pat. No. 16,248), 'MNIHAR015' has a broader and slower growth habit (40.64 cm and a spread of 71.12 cm in five years) than 'Roblen' which has a height of 91.44 cm and a spread of 60.96 cm in six years. Additionally, 'MNIHAR015' produces dark pink flowers, while 'Roblen' has bright red flowers.

I claim:

1. A new variety of Azalea plant named 'MNIHAR015' as herein shown and described.

* * * * *